United States Patent
Xu et al.

(10) Patent No.: US 11,944,485 B2
(45) Date of Patent: Apr. 2, 2024

(54) ULTRASOUND DEVICE, SYSTEMS, AND METHODS FOR LUNG PULSE DETECTION BY PLUERAL LINE MOVEMENT

(71) Applicant: KONINKLIJKE PHILIPS N.V., Eindhoven (NL)

(72) Inventors: Jingping Xu, Shanghai (CN); Balasundar Iyyavu Raju, North Andover, MA (US); Shougang Wang, Ossining, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 454 days.

(21) Appl. No.: 17/263,274

(22) PCT Filed: Jul. 24, 2019

(86) PCT No.: PCT/EP2019/069860
§ 371 (c)(1),
(2) Date: Jan. 26, 2021

(87) PCT Pub. No.: WO2020/020920
PCT Pub. Date: Jan. 30, 2020

(65) Prior Publication Data
US 2021/0298715 A1   Sep. 30, 2021

Related U.S. Application Data

(60) Provisional application No. 62/712,016, filed on Jul. 30, 2018.

(30) Foreign Application Priority Data

Jul. 27, 2018 (WO) ................ PCT/CN2018/097534

(51) Int. Cl.
*A61B 8/08* (2006.01)
*A61B 8/00* (2006.01)
(Continued)

(52) U.S. Cl.
CPC ................ *A61B 8/08* (2013.01); *A61B 8/461* (2013.01); *A61B 8/486* (2013.01);
(Continued)

(58) Field of Classification Search
CPC ...................... A61B 8/486; G06T 2207/20224
See application file for complete search history.

(56) References Cited

U.S. PATENT DOCUMENTS

| 4,173,007 A | 10/1979 | Buchin et al. |
| 5,899,864 A * | 5/1999 | Arenson ............. G01S 7/52071 600/455 |

(Continued)

FOREIGN PATENT DOCUMENTS

| WO | 2015048767 A1 | 4/2015 | |
| WO | 2017162860 A1 | 9/2017 | |
| WO | WO-2018124173 A1 * | 7/2018 | ............... A61B 5/08 |

OTHER PUBLICATIONS

WO-2018124173-A1 (Year: 2018).*
(Continued)

*Primary Examiner* — Joel Lamprecht
*Assistant Examiner* — Nyrobi Celestine

(57) ABSTRACT

Systems, devices, and methods for automated, fast lung pulse detection are provided. In an embodiment, a system for detecting pneumothorax (PTX) includes an ultrasound probe in communication with a processor. The processor is configured to generate, using the ultrasound imaging data received from the ultrasound probe, an M-mode image including a pleural line of the lung. Using the M-mode image, the processor generates a difference image comprising a plurality of difference lines generated by subtracting adjacent samples of the M-mode image. The processor analyzes the difference image to determine whether the difference image includes a periodic signal corresponding to the heartbeat of the patient and outputs a graphical repre-
(Continued)

sentation of detecting the lung pulse based on determining that the difference image includes the periodic signal corresponding to the heartbeat.

20 Claims, 11 Drawing Sheets

(51) Int. Cl.
  *G01S 7/52* (2006.01)
  *G01S 15/89* (2006.01)
  *G06T 7/00* (2017.01)

(52) U.S. Cl.
  CPC ...... *G01S 7/52053* (2013.01); *G01S 15/8915* (2013.01); *G06T 7/0016* (2013.01); *G06T 2207/10132* (2013.01); *G06T 2207/20072* (2013.01); *G06T 2207/20104* (2013.01); *G06T 2207/20224* (2013.01); *G06T 2207/30061* (2013.01)

(56) References Cited

U.S. PATENT DOCUMENTS

| | | | | |
|---|---|---|---|---|
| 2009/0214093 A1* | 8/2009 | Yao | .......................... | A61B 8/08 |
| | | | | 382/128 |
| 2013/0184584 A1* | 7/2013 | Berkey | ................ | A61B 8/5292 |
| | | | | 600/441 |
| 2015/0011883 A1* | 1/2015 | Belt | ........................ | A61B 8/461 |
| | | | | 600/443 |
| 2017/0090675 A1* | 3/2017 | Lee | ......................... | A61B 8/469 |
| 2017/0091914 A1 | 3/2017 | Halmann et al. | | |

OTHER PUBLICATIONS

Davis et al: "Ultrasound of the Lung";, Atlas of Emergency Ultrasound, Chapter 4, Edited by J. Christian Fox, 2011, pp. 35-57.
Gargani et al: "How I Do It:Lung Ultrasound"; Cardiovascular Ultrasound 2014, vol. 12:25, pp. 1-10.
Kristensen et al: "Ultrasonography for Clinical Decision-Making and Intervention in Airway Management: From the Mouth to the Lungs and Pleurae"; Insights Imaging (2014), vol. 5, pp. 253-279.
McClean et al.: "Ultrasound Determination of Chest Wall Thickness:Implications for Needle Thoracostomy"; American Journal of Emergency Medicine, (2011), vol. 29, pp. 1173-1177.
PCT/EP2019//069860 ISR & WO, dated Nov. 19, 2019, 15 Page Document.
Saul et al: "M-Mode Ultrasound Applications for the Emergency Medicine Physician"; Journal of Emergency Medicine, vol. 49, No. 5, pp. 686-692, 2015.
Via et al: "Lung Ultrasound in the ICU:From Diagnostic Instrument to Respiratory Monitoring Tool"; Minerva Anestesiologica, Nov. 2012, pp. 1282-1296.
Volpicelli et al: "International Evidence-Based Recommendations for Point-of-Care Lung Ultrasound"; Intensive Care Med (2012), vol. 28, pp. 577-591.

* cited by examiner

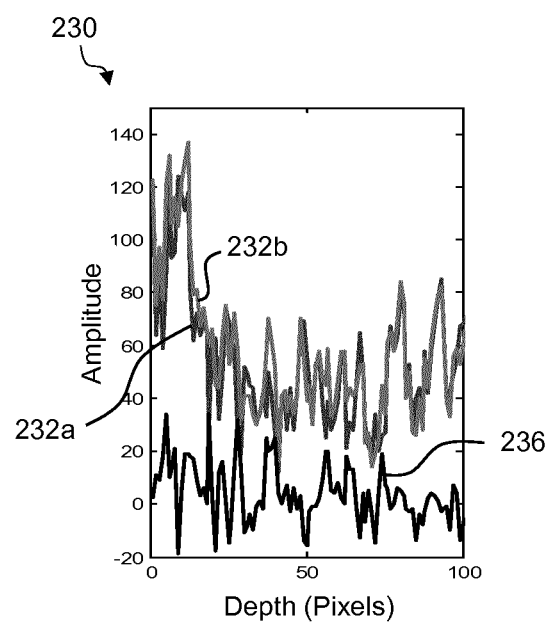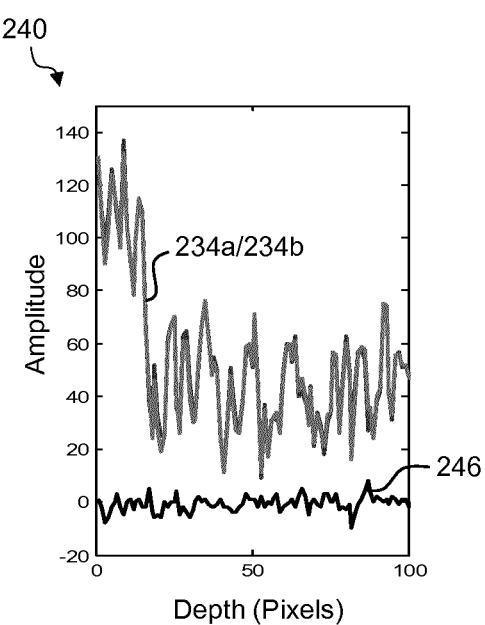
FIG. 4A
FIG. 4B

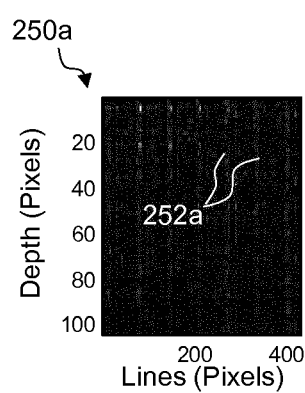
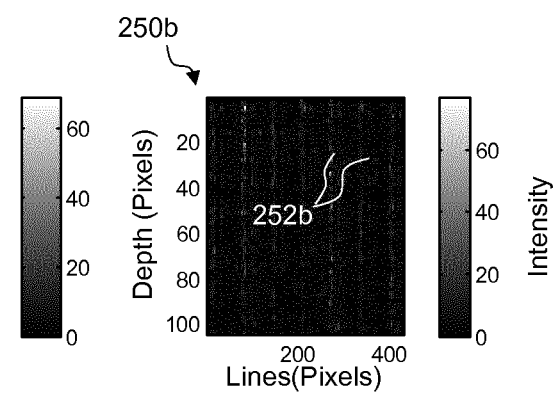
FIG. 5A    FIG. 5B
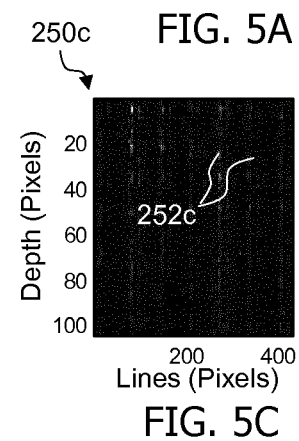
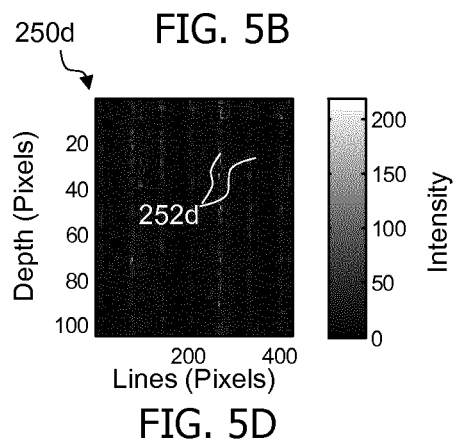
FIG. 5C    FIG. 5D

ULTRASOUND DEVICE, SYSTEMS, AND METHODS FOR LUNG PULSE DETECTION BY PLUERAL LINE MOVEMENT

CROSS-REFERENCE TO PRIOR APPLICATIONS

This application is the U.S. National Phase application under 35 U.S.C. § 371 of International Application No. PCT/EP2019/069860, filed on Jul. 24, 2019, which claims the benefit China Patent Application No. PCT/CN2018/097534, filed on Jul. 27, 2018, and U.S. Provisional Patent Application No. 62/712,016, filed on Jul. 30, 2018. These applications are hereby incorporated by reference herein.

TECHNICAL FIELD

The present disclosure relates generally to ultrasound systems and methods for obtaining ultrasound images of an anatomy. For example, an ultrasound system can identify or detect a lung pulse in an image obtained by an ultrasound imaging device.

BACKGROUND

Ultrasound imaging is frequently used to obtain images of internal anatomical structures of a patient. Ultrasound systems typically comprise an ultrasound transducer probe that includes one or more ultrasound transducer elements. An ultrasound transducer element is activated to vibrate at ultrasonic frequencies to transmit ultrasonic energy into the patient's anatomy, and then receive ultrasonic echoes reflected or backscattered by the patient's anatomy to create an image. Each transmit/receive cycle may produce a single scan, or line, of imaging data. By incrementally changing the scanning direction, a two-dimensional image can be compiled from the series of scans, sometimes referred to as A-line scans. The two-dimensional image compiled from the series of A-line scans can be referred to as a B-mode image. This process of compiling B-mode images from a series of A-line scans can be repeated several times a second (e.g., 30/s) to create a live view of the imaged anatomy. When transmit position/direction is fixed at one position to acquire several A-lines over a period of time, these A-lines are used to create an M-mode image. Similarly, M-mode images can be generated from a B-mode image sequence if the ultrasound probe-transducer is fixed and kept still at a position during the ultrasound examination.

Ultrasound probes can be used to diagnose pneumothorax (PTX), or a collapsed lung caused by a collection of air in the pleural space between the lung and the chest wall. To diagnose PTX, an ultrasound transducer (e.g., a high frequency linear array transducer or curved array transducer) is positioned at the most anterior point of the patient's chest to identify the pleural line. This line appears as an echogenic horizontal line, located approximately a half-centimeter deeper than the shallowest extent of the ribs. The pleural line consists of the closely opposed visceral and parietal pleura. In a normal lung, the visceral pleura can be seen sliding back and forth against the parietal pleura producing a physiological phenomenon called "lung sliding", with a glistening or shimmering appearance as the subject breathes. B-line or B-lines artifacts (also called 'comet-tail' artifacts) are vertical hyperechoic lines that may extend posteriorly from the opposed pleura to the bottom of the screen or maximum imaging depth. The characteristics of the B-lines, such as the number, width, and/or intensity of the B-lines, change as the patient breathes.

Another useful indicator of PTX is the presence or absence of lung pulse. Lung pulse can be described as a discrete movement of the pleural line, in synchrony with the patient's heartbeat. This occurs due to transmission of heart movements to the lung and the visceral pleura. Lung pulse can only be seen when the two pleural blades are in contact with each other, therefore the presence of lung pulse, like lung sliding and B-lines, also rules out PTX.

Because lung pulse is usually generated from transmission of both the systolic and diastolic portions of the heartbeat, the lung pulse is usually a relative weak pulse signal within a strong background of tissue due to the subtle rhythmic movement of the visceral pleura upon the parietal pleura with cardiac oscillations. Visual ultrasonography is currently used in determining if there is any lung pulse in the M-mode image or B-mode image sequence of the chest. However, determining lung pulse by emergency physicians is a time-consuming process, and interpretation of ultrasound images of the chest by emergency physicians is subjective, especially when the heartbeat is weak or the position of the ultrasound probe is not in the optimal location (e.g., not close to the heart).

SUMMARY

The present disclosure provides systems, devices, and methods for automated, fast lung pulse detection approach with low computing load that utilizes the dynamic properties of an ultrasound image sequence to detect lung pulse. In an embodiment, a system for detecting PTX includes an ultrasound probe in communication with a processor. The ultrasound probe can be controlled by the processor and configured to obtain ultrasound imaging data to create an M-mode image, or an M-mode image reconstructed from a B-mode image sequence, of a patient's chest. The processor can be configured to analyze the M-mode image, or reconstructed B-mode image, to detect the presence of a lung pulse. If the processor detects a lung pulse, the system can output a graphical representation of the presence/absence of the lung pulse to a display. The embodiments of the present disclosure are especially useful for difficult cases where the lung pulse is unclear visually at a single frame of M-mode image or B-mode image sequence.

According to one embodiment, a system for detecting a lung pulse in a patient comprises an ultrasound probe configured to obtain ultrasound imaging data representative of a lung of the patient and a processor communicatively coupled to the ultrasound probe. The processor is configured to generate, using the ultrasound imaging data received from the ultrasound probe, an M-mode image including a pleural line of the lung. The M-mode image comprises a plurality of samples obtained along a scan line. The processor is further configured to generate, from the M-mode image, a difference image comprising a plurality of difference lines generated by subtracting adjacent samples of the M-mode image, each of the plurality of difference lines comprising a plurality of intensity values along an axial direction. The processor is further configured to analyze the difference image to determine whether the difference image includes a periodic signal corresponding to the heartbeat of the patient, and output, to a display in communication with the processor, a graphical representation of detecting the lung pulse based on determining that the difference image includes the periodic signal corresponding to the heartbeat.

In some embodiments, the processor is configured to determine a location of the pleural line in the M-mode image. In some embodiments, the processor is configured to analyze the difference image to determine whether the difference image includes the periodic signal by generating an axial intensity curve by summing the plurality of intensity values in each of the plurality of difference lines along the axial direction, and determining whether the axial intensity curve includes the periodic signal corresponding to the heartbeat of the patient. The processor can determine whether the axial intensity curve includes the periodic signal corresponding to the heartbeat by applying an autocorrelation function to the axial intensity curve.

In some embodiments, the processor is configured to generate the M-mode image from the scan line in each of a plurality of B-mode images obtained by the ultrasound probe over a period of time. In other embodiments, the processor is configured to control the ultrasound probe to operate in an M-mode to generate the M-mode image. In some aspects, the plurality of difference lines comprises a plurality of first-order difference lines generated by subtracting immediately adjacent samples in the M-mode image. In another aspect, the plurality of difference lines comprises a plurality of (n)-order difference lines generated by subtracting adjacent (n−1)-order difference lines.

In some embodiments, the system further comprises the display, wherein the graphical representation indicates at least one of a presence of the lung pulse or a period of the lung pulse. The graphical representation can include a marker overlaid on the M-mode image identifying a location of the lung pulse on the M-mode image. In another aspect, the system further comprises a user interface device communicatively coupled to the processor, and wherein the processor is configured to receive a user input, from the user interface device, identifying a region of interest in the M-mode image, and generate the difference image for the region of interest in the M-mode image identified by the user input.

In another aspect of the present disclosure, a method for detecting a lung pulse in a patient comprises obtaining, by an ultrasound probe, ultrasound imaging data representative of a lung of the patient, generating, by a processor communicatively coupled to the ultrasound probe and using the ultrasound imaging data received from the ultrasound probe, an M-mode image including a pleural line of the lung, the M-mode image comprising a plurality of samples obtained along a scan line, generating, by the processor, a difference image from the M-mode image, the difference image comprising a plurality of difference lines generated by subtracting adjacent samples of the M-mode image, each of the plurality of difference lines comprising a plurality of intensity values along an axial direction, determining, by the processor, whether the difference image includes a periodic signal corresponding to a heartbeat of the patient, and outputting, to a display in communication with the processor, a graphical representation of detecting the lung pulse based on determining that the difference image includes the periodic signal corresponding to the heartbeat.

In some embodiments, the method further comprises determining, by the processor, a location of the pleural line in the M-mode image. In some embodiments, the step of determining, by the processor, whether the difference image includes the periodic signal comprises generating, by the processor, an axial intensity curve by summing the plurality of intensity values in each of the plurality of difference lines along the axial direction, and determining, by the processor, whether the axial intensity curve includes a periodic signal corresponding to a heartbeat of the patient. In some embodiments, the method further comprises determining, by the processor, whether the axial intensity curve includes the periodic signal corresponding to the heartbeat by applying an autocorrelation function to the axial intensity curve.

In some embodiments, generating the M-mode image comprises generating the M-mode image from the scan line in each of a plurality of B-mode images obtained by the ultrasound probe over a period of time. In some aspects, obtaining the ultrasound imaging data representative of the lung of the patient comprises controlling, by the processor, the ultrasound probe to operate in an M-mode to generate the M-mode image. In other aspects, generating the difference image from the M-mode image comprises generating a plurality of first-order difference lines by subtracting immediately adjacent samples in the M-mode image. In some embodiments, generating the difference image from the M-mode image comprises generating a plurality of (n)-order difference lines by subtracting adjacent (n−1)-order difference lines. In some embodiments, outputting the graphical representation to the display includes indicating at least one of a presence of the lung pulse or a period of the lung pulse. In some aspects, the graphical representation comprises a marker overlaid on the M-mode image, the marker identifying a location of the lung pulse on the M-mode image. In another aspect, generating the difference image comprises receiving, at a user interface device in communication with the processor, a user input identifying a region of interest in the M-mode image, and generating the difference image for the region of interest in the M-mode image identified by the user input.

Additional aspects, features, and advantages of the present disclosure will become apparent from the following detailed description.

BRIEF DESCRIPTION OF THE DRAWINGS

Illustrative embodiments of the present disclosure will be described with reference to the accompanying drawings, of which:

FIG. 4A is a graphical view of two neighboring sample lines of an M-mode image and a corresponding difference line generated from the two sample lines, according to aspects of the present disclosure.

FIG. 4B is a graphical view of two neighboring sample lines of an M-mode image different from those of FIG. 4A and a corresponding difference line generated from the two sample lines, according to aspects of the present disclosure.

FIGS. 5A, 5B, 5C and 5D are illustrations of difference images in the first order, second order, third order, and fourth order, respectively, according to aspects of the present disclosure.

DETAILED DESCRIPTION

Figure 1:
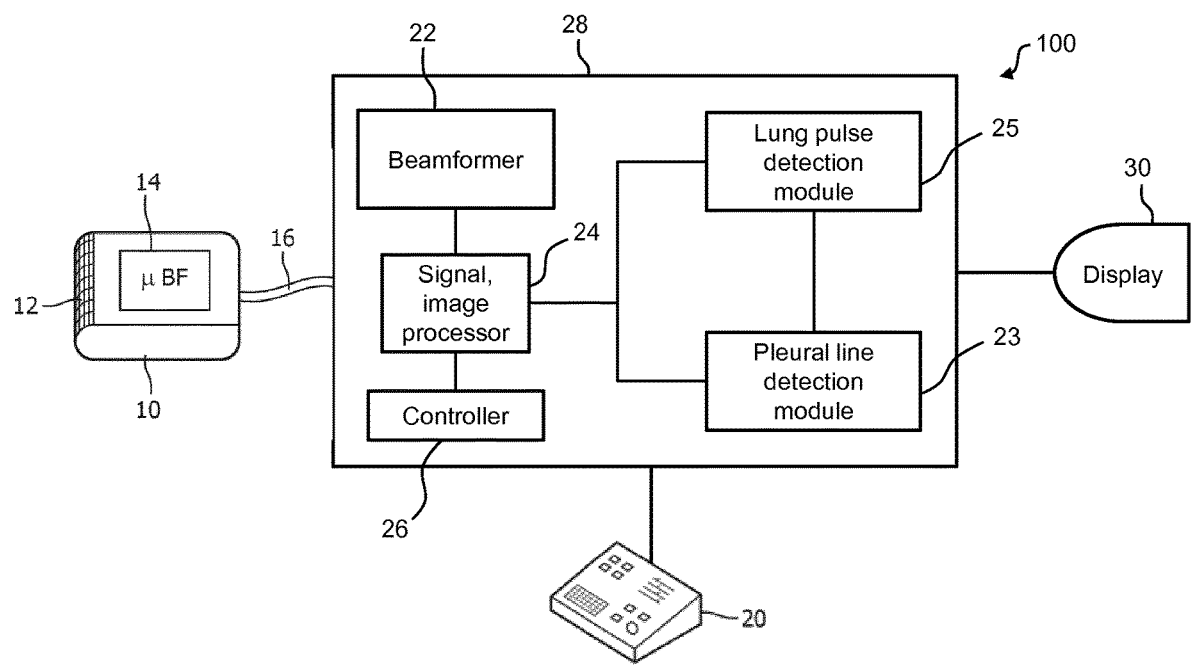
FIG. 1 is a diagrammatic schematic view of an ultrasound imaging system, according to aspects of the present disclosure.

For the purposes of promoting an understanding of the principles of the present disclosure, reference will now be made to the embodiments illustrated in the drawings, and specific language will be used to describe the same. It is nevertheless understood that no limitation to the scope of the disclosure is intended. Any alterations and further modifications to the described devices, systems, and methods, and any further application of the principles of the present disclosure are fully contemplated and included within the present disclosure as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. For the sake of brevity, however, the numerous iterations of these combinations will not be described separately.

In FIG. 1, an ultrasound system 100 according to embodiments of the present disclosure is shown in block diagram form. An ultrasound probe 10 has a transducer array 12 comprising a plurality of ultrasound transducer elements. In some instances, the array 12 may include any number of ultrasound transducer elements. For example, the array 12 can include between 1 transducer element and 1000 transducer elements, including values such as 2 transducer elements, 4 transducer elements, 36 transducer elements, 64 transducer elements, 128 transducer elements, 500 transducer elements, 812 transducer elements, and/or other values both larger and smaller. In some instances, the transducer elements of the array 12 may be arranged in any suitable configuration, such as a linear array, a planar array, a curved array, a curvilinear array, a circumferential array, an annular array, a phased array, a matrix array, a one-dimensional (1D) array, a 1.x dimensional array (e.g., a 1.5D array), or a two-dimensional (2D) array. The array of transducer elements (e.g., one or more rows, one or more columns, and/or one or more orientations) can be uniformly or independently controlled and activated. The array 12 can be configured to obtain one-dimensional, two-dimensional, and/or three-dimensional images of patient anatomy.

The ultrasound transducer elements may comprise piezoelectric/piezoresistive elements, piezoelectric micromachined ultrasound transducer (PMUT) elements, capacitive micromachined ultrasound transducer (CMUT) elements, and/or any other suitable type of ultrasound transducer elements. The ultrasound transducer elements of the array 12 are in communication with (e.g., electrically coupled to) electronic circuitry 14. In some embodiments, such as the embodiment of FIG. 1, the electronic circuitry 14 can comprise a microbeamformer (μBF). In other embodiments, the electronic circuitry comprises a multiplexer circuit (MUX). The electronic circuitry 14 is located in the probe 10 and communicatively coupled to the transducer array 12. In some embodiments, one or more components of the electronic circuitry 14 can be positioned in the probe 10. In some embodiments, one or more components of the electronic circuitry 14, can be positioned in a processor 28, or processing system. In some aspects, some components of the electronic circuitry 14 are positioned in the probe 10 and other components of the electronic circuitry 14 are positioned in the processor 28. The electronic circuitry 14 may comprise one or more electrical switches, transistors, programmable logic devices, or other electronic components configured to combine and/or continuously switch between a plurality of inputs to transmit signals from each of the plurality of inputs across one or more common communication channels. The electronic circuitry 14 may be coupled to elements of the array 12 by a plurality of communication channels. The electronic circuitry 14 is coupled to a cable 16, which transmits signals including ultrasound imaging data to the processor 28.

In the processor 28, the signals are digitized and coupled to channels of a system beamformer 22, which appropriately delays each signal. The delayed signals are then combined to form a coherent steered and focused receive beam. System beamformers may comprise electronic hardware components, hardware controlled by software, or a microprocessor executing beamforming algorithms. In that regard, the beamformer 22 may be referenced as electronic circuitry. In some embodiments, the beamformer 22 can be a system beamformer, such as the system beamformer 22 of FIG. 1, or it may be a beamformer implemented by circuitry within the ultrasound probe 10. In some embodiments, the system beamformer 22 works in conjunction with a microbeamformer (e.g., electronic circuitry 14) disposed within the probe 10. The beamformer 22 can be an analog beamformer in some embodiments, or a digital beamformer in some embodiments. In the case of a digital beamformer, the system includes A/D converters which convert analog signals from the array 12 into sampled digital echo data. The beamformer 22 generally will include one or more microprocessors, shift registers, and or digital or analog memories to process the echo data into coherent echo signal data. Delays are effected by various means such as by the time of sampling of received signals, the write/read interval of data temporarily stored in memory, or by the length or clock rate of a shift register as described in U.S. Pat. No. 4,173,007 to McKeighen et al., the entirety of which is hereby incorporated by reference herein. Additionally, in some embodiments, the beamformer can apply appropriate weight to each of the signals generated by the array 12. The beamformed signals from the image field are processed by a signal and image processor 24 to produce 2D or 3D images for display on an image display 30. The signal and image processor 24 may comprise electronic hardware components, hardware controlled by software, or a microprocessor executing image processing algorithms. It generally will also include specialized hardware or software which processes received echo data into image data for images of a desired display format such as a scan converter. In some embodiments, beamforming functions can be divided between different beamforming components. For example, in some embodiments, the system 100 can include a microbeamformer located within the probe 10 and in communication with the system beamformer 22. The microbeamformer may perform preliminary beamforming and/or signal processing that can reduce the number of communication channels required to transmit the receive signals to the processor 28.

Control of ultrasound system parameters such as scanning mode (e.g., B-mode, M-mode), probe selection, beam steering and focusing, and signal and image processing is done under control of a system controller 26 which is coupled to various modules of the system 100. The system controller 26 may be formed by application specific integrated circuits (ASICs) or microprocessor circuitry and software data storage devices such as RAMs, ROMs, or disk drives. In the case of the probe 10, some of this control information may be provided to the electronic circuitry 14 from the processor 28 over the cable 16, conditioning the electronic circuitry 14 for operation of the array as required for the particular scanning procedure. The user inputs these operating parameters by means of a user interface device 20.

In some embodiments, the image processor 24 is configured to generate images of different modes to be further analyzed or output to the display 30. For example, in some embodiments, the image processor can be configured to compile a B-mode image, such as a live B-mode image, of an anatomy of the patient. In other embodiments, the image processor 24 is configured to generate or compile an M-mode image. An M-mode image can be described as an image showing temporal changes in the imaged anatomy along a single scan line. The M-mode image can comprise a plurality of samples, each sample including a line of ultrasound imaging data obtained at a particular time. In that regard, the M-mode image shows ultrasound imaging data obtained along the scan line over a period of time, with each sample obtained at a different time. For example, as shown in FIG. 3, an M-mode image can show a plurality of samples along the x-axis, where each sample shows an intensity or amplitude as a function of depth on the y-axis, the amplitude represented by varying shades applied to each pixel of depth along the scan line. In some embodiments, the probe 10 can be controlled by the processor to operate in an M-mode to obtain the M-mode image. In other embodiments, the M-mode image can be compiled, reconstructed, or generated using a plurality of B-mode image frames. In some embodiments, the M-mode image includes ultrasound imaging data obtained for at least one heart cycle. In some embodiments, the M-mode image includes ultrasound imaging data obtained for several heart cycles, such as 5, 10, 15, or more heart cycles.

The processor 28 includes a pleural line detection module 23 and a lung pulse detection module 25. The pleural line detection module can be configured to analyze processed ultrasound imaging data from the image processor 24 to identify, or detect, a pleural line in the image. The pleural line detection module can identify the pleural line in a B-mode image and/or an M-mode image. In an exemplary embodiment, as will be further described below, the pleural line detection module is configured to identify both the presence and location of a pleural line in an M-mode image. For example, WO2017/162860 to Wang, et al., which is hereby incorporated by reference, provides exemplary systems, devices, and methods for the automated detection of pleural lines.

The lung pulse detection module 25 is configured to analyze the processed ultrasound image, such as an M-mode image, to identify one or more lung pulses in the image. As will be further explained below, the lung pulse detection module 25 can identify periodic dynamic changes in the imaged anatomy over a period of time in an M-mode image by comparing neighboring samples of the M-mode image. In some embodiments, when a lung pulse is detected, a visual indicator or graphical representation indicating the presence and/or location of the lung pulse on the M-mode image can be output to the display 30.

It will be understood that various components of the processor 28, such as the pleural line detection module 23 and/or the lung pulse detection module 25, can be carried out by a computing device, such as a computer processor in communication with a computer-readable memory device comprising computer-readable instructions to carry out the functions of the various components of the processor 28. Thus, the processor 28 can comprise hardware, such as a computer processor, application-specific integrated circuit (ASIC), field-programmable gate array (FPGA), capacitors, resistors, and/or other electronic devices, software, or a combination of hardware and software. In some embodiments, each component or module of the processor 28 is performed by a single computing device. In other embodiments, the various components of the processor 28 (e.g., modules 23, 25, beamformer 22, signal and image processor 24, etc.) are performed by separate computer devices in communication with one another.

Figure 2:
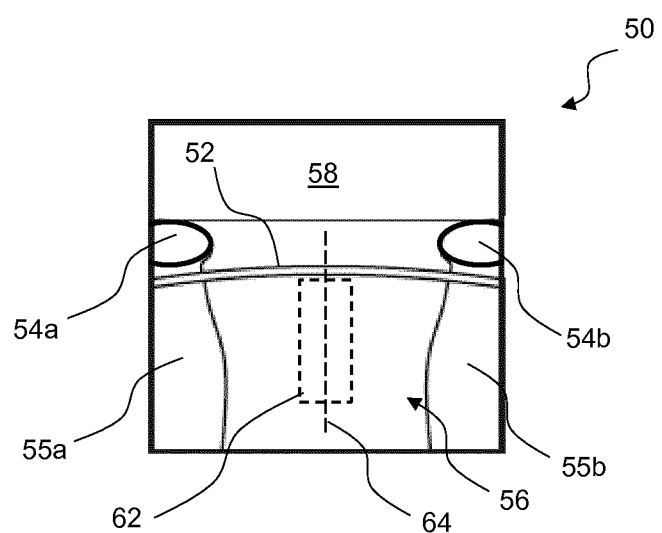
FIG. 2 is a diagrammatic view of an ultrasound image including a pleural line of a patient, according to aspects of the present disclosure.

FIG. 2 shows an illustration of two-dimensional ultrasound image 50 of the chest and/or abdomen of a patient obtained by an ultrasound probe. The ultrasound probe is positioned with respect to the patient to obtain ultrasound imaging data along an axial direction, represented by the scan line 64, to include imaging data of a pleural line 52. The axial direction can correspond to a direction of propagation of a lung pulse. In other words, the ultrasound probe can obtain ultrasound imaging data of a lung pulse by imaging along the axial direction. The image 50 shows a superior rib 54a and an inferior rib 54b are seen for a normal lung. At greater imaging depth, shadows 55a, 55b result from the ultrasound absorption by the ribs 54a, 54b. The pleural line 52, which is an anatomical landmark, includes, in a normal lung, a closely opposed parietal pleura and visceral pleura, represented by the two lines of the pleural line 52. A lung 56 is seen between the shadows 55a, 55b. The ribs 54a, 54b, and pleural line 52 can be imaged through superficial tissue 58 (e.g., skin) by an ultrasound probe.

In the case of a normal, or healthy, lung, a lung pulse can be observed as an oscillation of the lung tissue 56 in the area below the pleural line 52. Thus, the identification of a lung pulse can rule out PTX. In the case of PTX, the lung pulse may not propagate through the lung tissue 56 to the pleural line 52.

When an M-mode image is generated, various frames, or samples, of imaging data are obtained along a scan line 64. The scan line 64 intersects the pleural line 52 and continues into the lung 56. In some embodiments, in order to detect lung pulse, a region of interest 62 is selected along the scan line 64 that includes the lung tissue in an area below the pleural line 52. The region of interest 62 will be identified in a corresponding M-mode image obtained along the scan line 64 to identify a lung pulse.

Figure 3A:
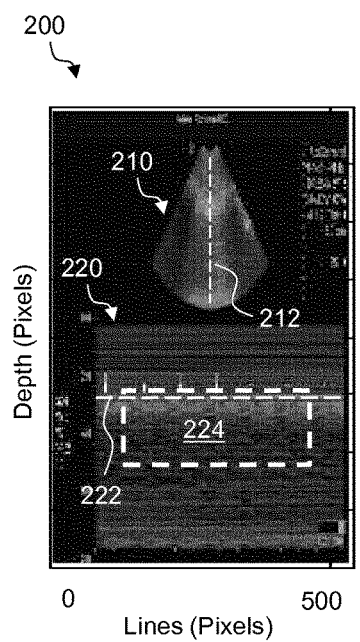
FIG. 3A is an illustration of a user interface of a lung pulse detection system, according to aspects of the present disclosure.
Figure 3B:
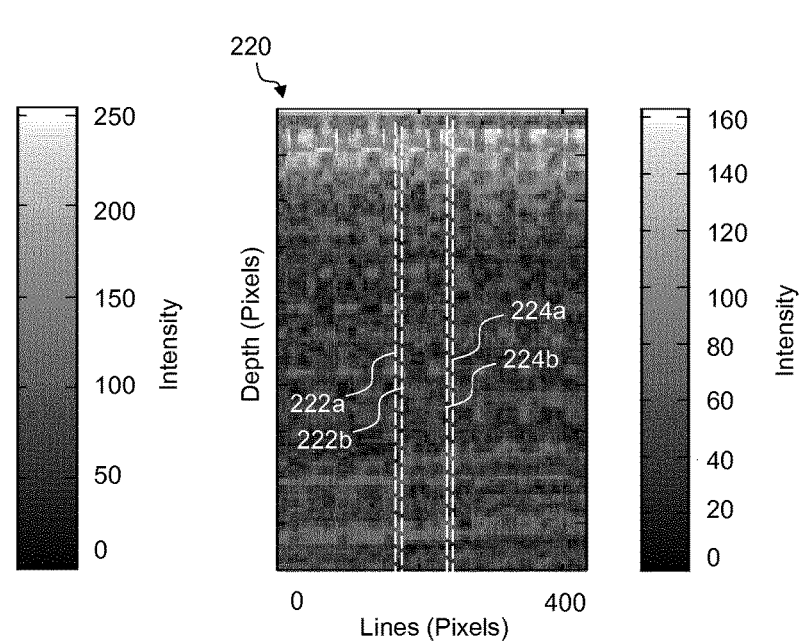
FIG. 3B is an illustration of an M-mode image of a region of interest, according to aspects of the present disclosure.
Figure 6A:
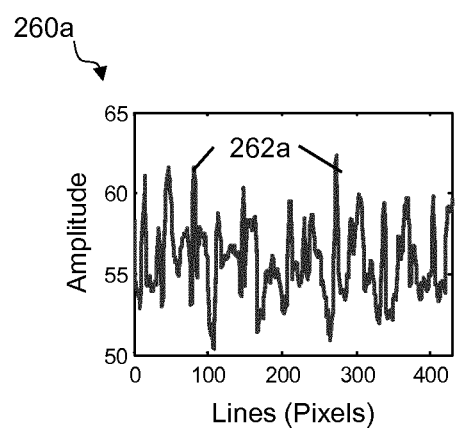
FIGS. 6A, 6B, 6C and 6D are graphical views of axial intensity curves generated from the difference images shown in FIGS. 5A, 5B, 5C and 5D, according to aspects of the present disclosure.
Figure 6B:
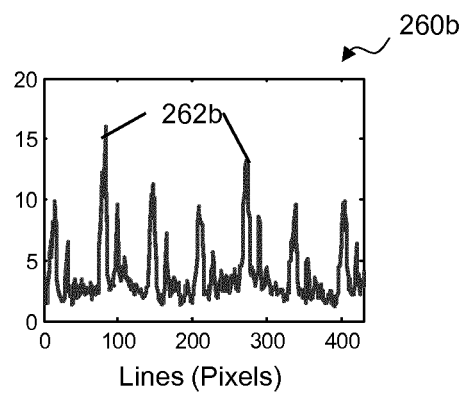
Figure 6C:
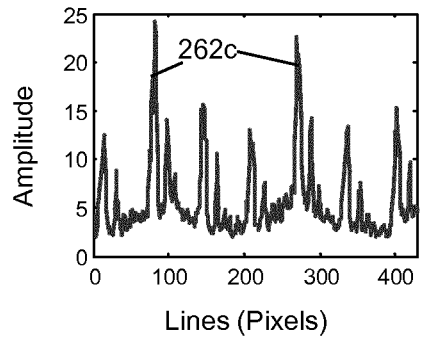
Figure 6D:
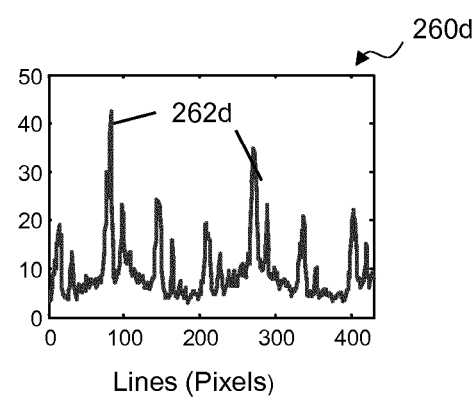

FIGS. 3A and 3B depicts a user interface 200 of an ultrasound imaging system, the user interface 200 showing a B-mode image and an M-mode image. Portions of FIGS. 3A and 3B include aspects from J. Davis and S. Cusik, "Ultrasound of the Lung" in Atlas of Emergency Ultrasound, pp. 35-37 (J. Christian Fox, ed., 2011), the entirety of which is hereby incorporated by reference. FIG. 3A depicts a user interface 200 of a lung pulse detection system, according to some embodiments of the present disclosure. The interface 200 includes a B-mode image 210 of a lung, and an M-mode image 220 obtained along a scan line 212. In some embodiments, the M-mode image 220 is compiled, reconstructed, or generated from a plurality of B-mode image frames obtained over a period of time, and may represent a plurality of samples. By compiling or reconstructing the M-mode image from a plurality of B-mode image frames, a field of view larger than a single scan line can be imaged, which may improve the efficiency of the examination procedure. Each sample can be described as a single A-line of ultrasound imaging data obtained along a scan line 212. For example, a B-mode image comprises a plurality of A-line scans obtained across a field of view by sweeping the scan line across the field of view. By contrast, an M-mode image includes a plurality of A-line scans obtained over a period of time along a same scan line, or same direction, such as scan line 212.

The M-mode image 220 shows a pleural line 222. In some embodiments, the pleural line 222 can be automatically identified by a processor (e.g., a pleural line detection module). A region of interest (ROI) 224 is selected in the M-mode image 220 including an area below the pleural line 222. In the embodiment of FIG. 3A, the ROI includes the pleural line 222. In other embodiments, the ROI may not include the pleural line 222.

FIG. 3B is an illustration of the M-mode image 220, according to some embodiments of the present disclosure. In FIG. 3B, the M-mode image 220 may include data representative of the ROI 224. The M-mode image 220 can include data from a plurality of samples obtained along the scan line 212. The M-mode image 220 includes approximately 400 samples. In other embodiments, the M-mode image 220 can include fewer or more samples, such as 50, 100, 500, 1,000, or more samples. Specifically, the M-mode image includes a first neighboring pair of samples 222a, 222b, and a second pair of neighboring samples, 224a, 224b. The neighboring samples can be immediately adjacent one another, or may be separated by one or more additional samples. Although the neighboring samples 222a, 222b, 224a, 224b, are shown as separated from one another for illustrative purposes, the neighboring samples 222a, 222b, 224a, 224b can be considered as immediately adjacent one another. As will be further discussed below, neighboring samples can be compared by, for example, subtraction, to generate a difference image to identify a lung pulse in the M-mode image 220.

While the x-axis designates discrete samples of the M-mode image, the y-axis illustrates an intensity or amplitude of a reflected ultrasound image at each pixel of depth in the tissue. In other words, the y-axis can be characterized as showing depth in the tissue measured by pixels, while the shade of each pixel in the M-mode image represents an intensity of the ultrasound signal at each pixel of depth.

FIG. 4A is a graph 230 showing plots 232a, 232b for neighboring samples 222a, and 222b, as shown in FIG. 3B. The graph 230 also includes a difference plot 236 generated by subtracting plot 232b from 232a. Likewise, FIG. 4B is a graph 240 showing plots 234a, 234b for neighboring samples 224a, 224b shown in FIG. 3B. The graph 240 also includes a difference plot 246 generated by subtracting plot 234b from 234a. Because each plot 232a, 232b, 234a, and 234b represents a single sample, the graphs 230 and 240 of FIGS. 4A and 4B include depth (pixels) on the x-axis, and amplitude or intensity on the y-axis, which is opposite of FIGS. 3A and 3B. Referring to FIG. 4A, the neighboring samples 222a, 222b represented by plots 232a, 232b, respectively, are obtained during a lung pulse. Thus, the difference plot 236 shows significant variation between the values of plots 232a and 232b. By contrast, in FIG. 4B, the neighboring samples 224a, 224b represented by plots 234a, 234b, were obtained between lung pulses at a time when the imaged anatomy was relatively stable, or motionless. Thus, the difference plot 246 of FIG. 4B shows relatively less variation between the values of plots 234a and 234b.

FIGS. 5A, 5B, 5C and 5D are difference images 250a, 250b, 250c, 250d generated by a lung pulse detection system based on the M-mode image 220. Each difference image 250a, 250b, 250c, 250d can be generated by subtracting neighboring samples (e.g., 222a, 222b), across the M-mode image. Subtracting neighboring samples in the M-mode image can remove from M-mode image unwanted information that reflects motionless tissue, and leaves information showing motion due to lung pulse along an axial direction. FIG. 5A is a first-order difference image 250a that includes first-order difference lines 252a generated by subtracting immediately adjacent samples from the M-mode image 220. The first-order difference lines 252a include dotted or dashed lines of relatively higher intensity, showing periodic motion of lung tissue due to lung pulse. FIG. 5B is a second-order difference image 250b that includes second-order difference lines 252b generated by subtracting immediately adjacent first-order difference lines 252a from the first-order difference image 250a. FIG. 5C is a third-order difference image 250c that includes third-order difference lines 252c generated by subtracting immediately adjacent second-order difference lines 252b from the second-order difference image 250b. FIG. 5D is a fourth-order difference image 250d that includes fourth-order difference lines 252d generated by subtracting immediately adjacent third-order difference lines 252c from the third-order difference image 250c. Higher-order difference images 250b, 250c and 250d can further reduce unwanted information from the M-mode image corresponding to motionless tissue to increase a signal-to-noise ratio (SNR) in a difference image to identify lung pulse motion in tissue. Although the difference lines 252a, 252b, 252c, and 252d indicated in FIGS. 5A-D are relatively noticeable in the difference images, it will be understood the difference images comprise a plurality of difference lines not indicated in the difference images. In other words, a difference image may comprise approximately as many difference lines as the original M-mode image comprises samples.

FIGS. 6A, 6B, 6C and 6D are axial intensity curves respectively generated from the difference images 250a, 250b, 250c, 250d of FIGS. 5A, 5B, 5C and 5D. Each axial intensity curve 260a, 260b, 260c, 260d can be generated by summing, along the axial direction, the intensity values for the difference lines in the corresponding difference image. In that regard, the peaks 262a, 262b, 262c, 262d, of the axial intensity curves may illustrate samples in which relatively greater motion occurred in the tissue. Accordingly, the peaks 262a, 262b, 262c, 262d of the axial intensity curves can illustrate the temporal locations of one or more lung pulses in the M-mode image.

Figure 7:
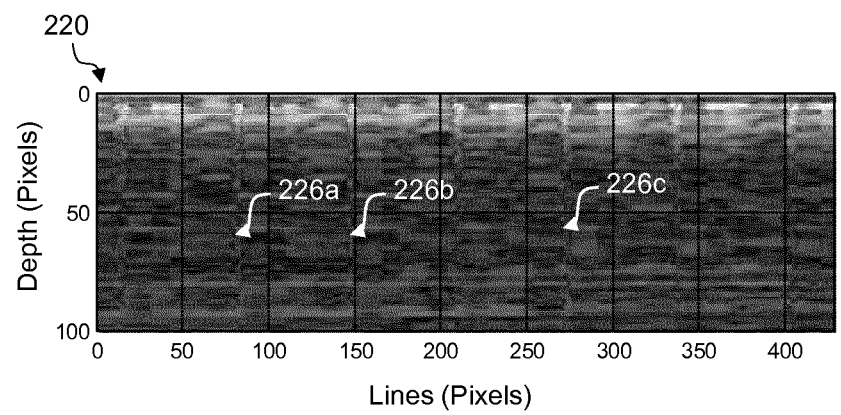
FIG. 7 is an illustration of an M-mode image shown lung pulses, according to aspects of the present disclosure.
Figure 8:
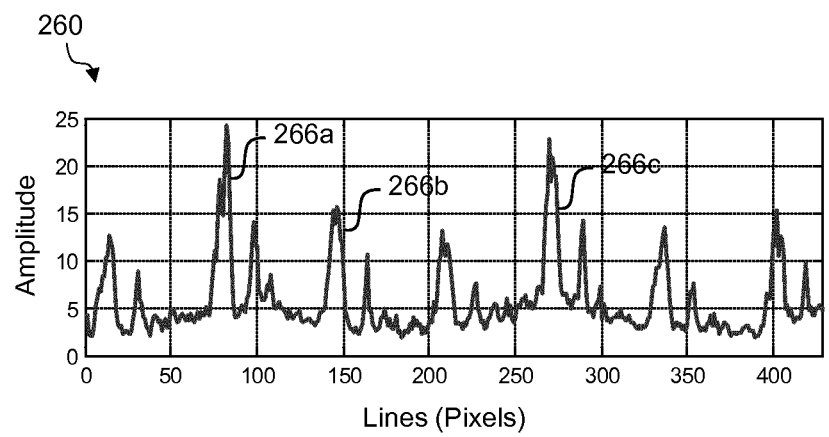
FIG. 8 is a graphical view of an axial intensity curve created from the M-mode image of FIG. 7, according to aspects of the present disclosure.

FIGS. 7 and 8 respectively show an M-mode image 220 including a plurality of lung pulses 226a, 226b, 226c, and an axial intensity curve plot 260 generated from the M-mode image 220. The axial intensity curve plot 260 of FIG. 8 can be generated by summing, in the axial direction, the intensity values of a third-order difference image, which can be compiled as described above with respect to FIG. 5C. As shown in FIGS. 7 and 8, the peaks 266a, 266b, and 266c, align with the locations (i.e. samples) of the corresponding lung pulses 226a, 226b, and 226c. As will be described further below, the axial intensity curve for an M-mode image can be further analyzed to determine whether a periodic motion can be identified having a period corresponding to a heartbeat of the patient.

Figure 9:
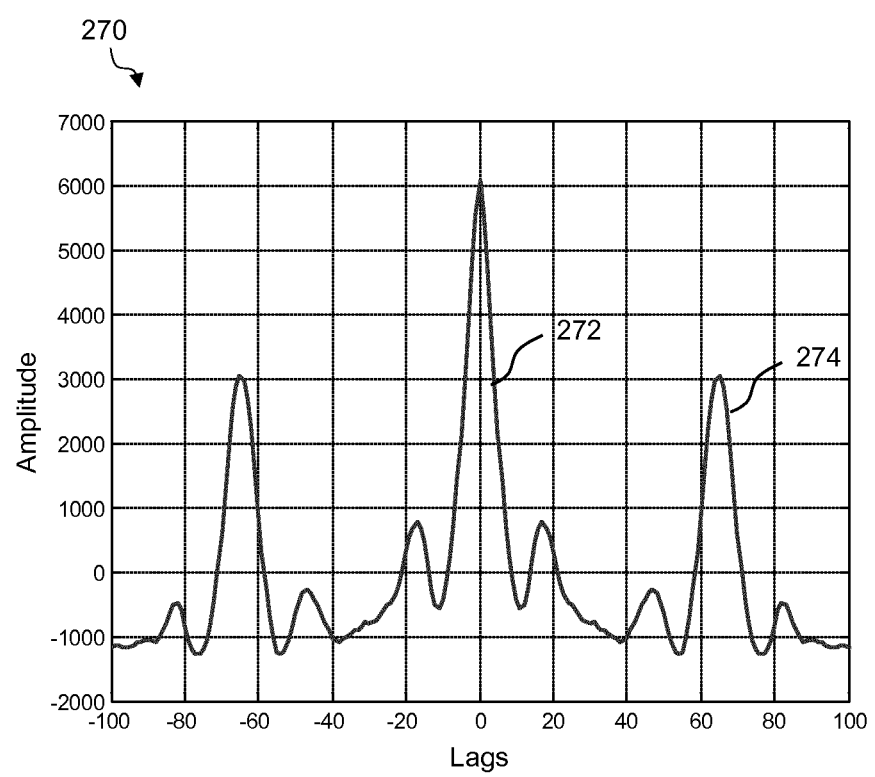
FIG. 9 is a graphical view of an autocorrelation function applied to the axial intensity curve of FIG. 8, according to some aspects of the present disclosure.

FIG. 9 is a graph 270 including an autocorrelation plot 272 generated by applying an autocorrelation function to thee axial intensity curve shown in plot 260 of FIG. 8. The autocorrelation function can be applied to the curve to identify regular, or periodic signals in the curve. In that regard, the autocorrelation function can be used to determine an average period of an axial intensity curve. In the plot 272 of FIG. 9, the autocorrelation function reveals a peak 274 representing a periodic increase in tissue motion (i.e., lung pulse) at approximately 65 lags. In some embodiments, lags may correspond to a number of samples in the M-mode image and/or the difference image. Thus, 65 lags may correspond to a heartbeat of the patient. In some embodiments, determining whether there is a periodic motion in the axial intensity curve includes applying knowledge-based rules. For example, the location, measured in lags, of the peak 274 can be compared to an actual measured heartbeat of the patient to verify that the periodic motion identified in the axial intensity curve is representative of the heartbeat, and thus the lung pulse, of the patient. In some embodiments, the actual heartbeat is measured by heart monitoring equipment, such as an electrocardiography system (ECG), or a heart pulse monitor.

Figure 10:
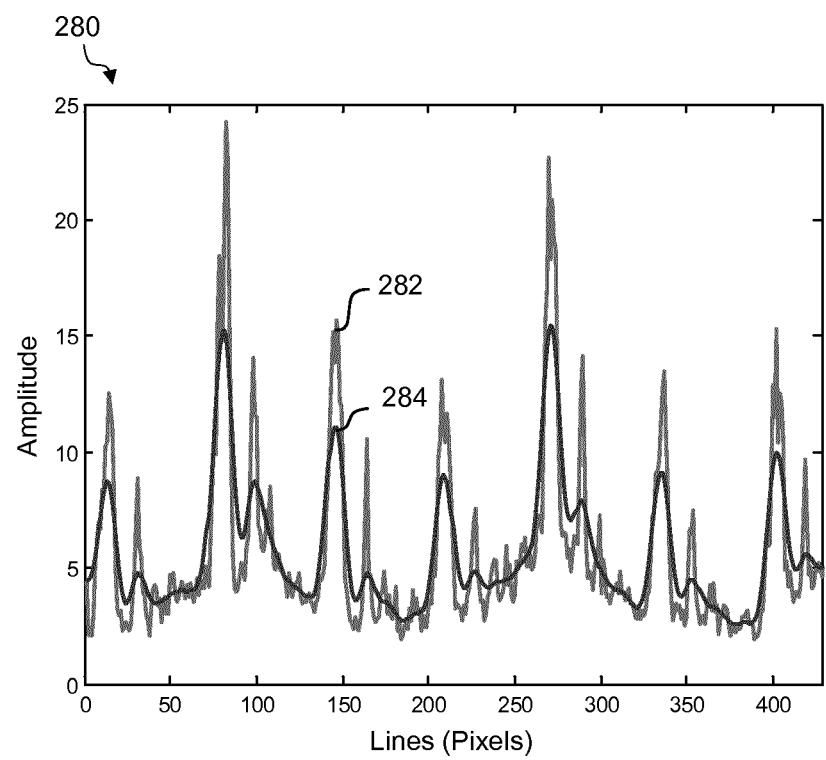
FIG. 10 is a graphical view of an axial intensity curve of an M-mode image and a corresponding smoothed axial intensity curve, according to aspects of the present disclosure.
Figure 11:
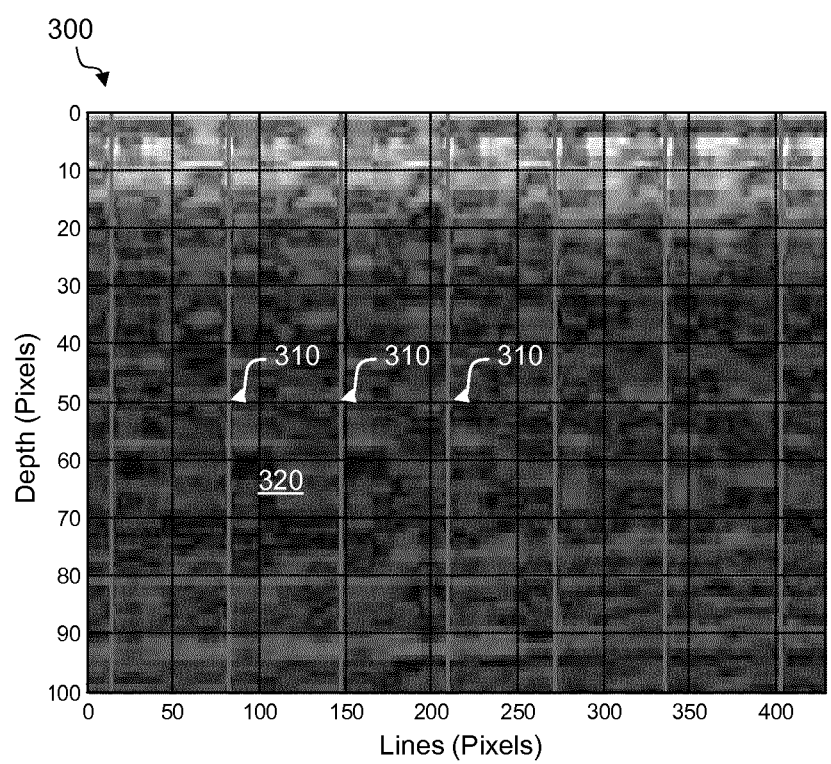
FIG. 11 is an illustration of an M-mode image with graphical representations of a lung pulse overlaid on the M-mode image, according to aspects of the present disclosure.

FIG. 10 is a graph 280 showing an axial intensity curve 282 and a corresponding smoothed axial intensity curve 284. In some embodiments, the smoothed curve 284 can be used with knowledge-based rules, as described above, to determine or identify a periodic signal in the axial intensity curve 282 representative of a lung pulse. For example, the smoothed curve 284 can be used together with an average period determined by the autocorrelation plot 272 to determine a location of each of a plurality of lung pulses in the original M-mode image. Once determined, the system, by the processor, can output a graphical representation of the lung pulse to the display. For example, FIG. 11 shows a user interface 300 that includes a plurality of lung-pulse identifying markers 310 overlaid on an M-mode image 320 showing the temporal location of the lung pulses. In other embodiments, the system may output other visual indications of the lung pulse, such as a green box or label to identify that lung pulse was detected, a numerical indicator representative of a period or frequency of the lung pulse, or any other suitable visual indicator. In some embodiments, when the system does not detect a lung pulse, a visual indicator can be output to the display to notify a user that no lung pulse was detected. In, other embodiments, the system can output to the display a visual indicator notifying the user that the lung pulse detection is inconclusive, that insufficient data was collected, an error occurred, and/or that a result cannot be confirmed.

Figure 12:
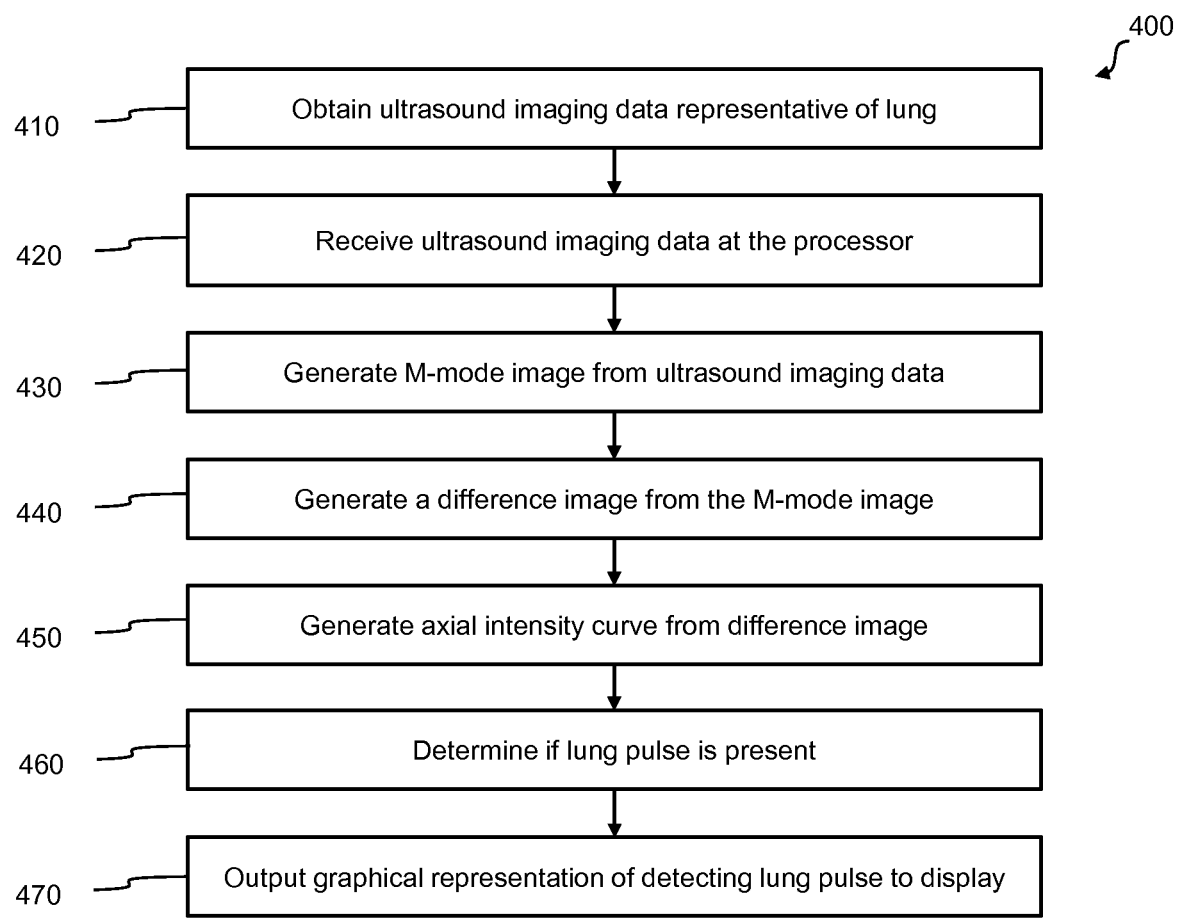
FIG. 12 is a flow diagram illustrating a method for detecting lung pulse by ultrasonography, according to aspects of the present disclosure.

FIG. 12 is a flow diagram illustrating a method 400 for detecting a lung pulse using an ultrasound system, according to some embodiments of the present disclosure. In step 410, ultrasound imaging data representative of a lung of a patient is obtained using an ultrasound probe positioned to obtain the imaging data along an axial direction. The axial direction may correspond to a direction of the propagation of the lung pulse. The ultrasound imaging data can include imaging data representative of a pleural line, in some instances. In step 420, the ultrasound imaging data is received by the processor. As described above, the processor can include a controller, a beamformer, a signal processor, an image processor, a pleural line detection module, and/or a lung pulse detection module. In step 430, an M-mode image is generated by the ultrasound probe and/or processor from the obtained ultrasound imaging data. In some embodiments, the ultrasound probe is controlled by the processor to operate in an M-mode to obtain M-mode data along a scan line. In other embodiments, the processor may control the ultrasound probe to operate in a B-mode to obtain a plurality of frames of B-mode data, and the processor may compile, generate, or reconstruct the M-mode data from the plurality of B-mode frames.

In step 440, the processor (e.g., the lung detection modules) can generate a difference image from the M-mode image. In some embodiments, generating the M-mode image comprises selecting, or identifying a region of interest (ROI) in the M-mode image below a pleural line. In some embodiments, identifying the region of interest includes identifying the pleural line in the image. The pleural line and/or the ROI can be identified automatically by a pleural line detection module, in some embodiments. Where the pleural line is detected automatically, the system may receive an input from a user indicating a pleural line region in an upper portion, or half, of the M-mode image to identify the pleural line. In other embodiments, the pleural line can be manually identified by a user input via a user interface device. The difference image can be generated by subtracting adjacent samples from the M-mode image. In some embodiments, immediately adjacent samples are subtracted. In other embodiments, distantly adjacent samples are subtracted.

In some embodiments, the difference image is a first-order difference image. In other embodiments, the difference image is a second-order difference image, a third-order difference image, a fourth-order difference image, or a higher-order difference image. In that regard, an (n)-order difference image can include a plurality of (n)-order difference lines generated by subtracting adjacent (n−1)-order difference lines. In step 450, an axial intensity curve is generated from the difference image by summing intensity values of each difference line of the difference image. In step 460, the processor determines, based on the axial intensity curve, if a period is identified in the axial intensity curve representative of a lung pulse. In some embodiments, step 460 includes applying an autocorrelation function to the axial intensity curve. In some embodiments, step 460 includes generating a smoothed axial intensity curve. In some embodiments, step 460 includes applying knowledge-based rules to the axial intensity curve to verify whether the detected period corresponds to the patient's heart beat.

In step 470, a graphical representation of detecting the lung pulse is output to a display. In some embodiments, the graphical representation comprises a marker overlaid on the M-mode image indicating a location of one or more lung pulses in the M-mode image. In some embodiments, the graphical indication indicates whether or not a lung pulse is detected. For example, a green-colored marker can indicate that a lung pulse was detected, while a red indicator can indicate that no lung pulse was detected. In other embodiments, the graphical representation can include a numerical indicator of an aspect of the lung pulse.

Persons skilled in the art will recognize that the apparatus, systems, and methods described above can be modified in various ways. Accordingly, persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. It is understood that such variations may be made to the foregoing without departing from the scope of the present disclosure. Accordingly, it is appropriate that the appended claims be construed broadly and in a manner consistent with the present disclosure.

What is claimed is:

1. A system for detecting a lung pulse in a patient, comprising:
    an ultrasound probe configured to obtain ultrasound imaging data representative of a lung of the patient; and
    a processor communicatively coupled to the ultrasound probe, the processor configured to:
        generate, using the ultrasound imaging data received from the ultrasound probe, an M-mode image including a pleural line of the lung, the M-mode image comprising a plurality of samples obtained along a scan line;
        generate, from the M-mode image, a difference image comprising a plurality of difference lines generated by subtracting adjacent samples of the M-mode image, each of the plurality of difference lines comprising a plurality of intensity values;
        analyze the difference image to determine whether the difference image includes a periodic signal representative of a lung pulse, wherein the lung pulse comprises a movement of a pleural line corresponding to a heartbeat of the patient; and
        output, to a display in communication with the processor, a graphical representation of detecting the lung pulse in response to determining that the difference image includes the periodic signal.

2. The system of claim 1, wherein the processor is configured to determine a location of the pleural line in the M-mode image.

3. The system of claim 1,
    wherein the difference image comprises a y-axis representative of a plurality of depths and an x-axis representative of the plurality of difference lines such that each difference line comprises a vertical line,
    wherein the plurality of intensity values is arranged along the vertical line,
    wherein the processor is configured to analyze the difference image to determine whether the difference image includes the periodic signal by:
        generating an axial intensity curve by summing, along each vertical line, the plurality of intensity values; and
        determining whether the axial intensity curve includes the periodic signal.

4. The system of claim 3, wherein the processor is configured to determine whether the axial intensity curve includes the periodic signal by applying an autocorrelation function to the axial intensity curve.

5. The system of claim 1, wherein the processor is configured to generate the M-mode image from the scan line in each of a plurality of B-mode images obtained by the ultrasound probe over a period of time.

6. The system of claim 1, wherein the processor is configured to control the ultrasound probe to operate in an M-mode to generate the M-mode image.

7. The system of claim 1, wherein the plurality of difference lines comprises a plurality of first-order difference lines generated by subtracting immediately adjacent samples in the M-mode image.

8. The system of claim 1, wherein the plurality of difference lines comprises a plurality of second-order difference lines generated by subtracting immediately adjacent samples in the difference image.

9. The system of claim 1, further comprising the display, wherein the graphical representation indicates at least one of a presence of the lung pulse or a period of the lung pulse.

10. The system of claim 9, wherein the graphical representation comprises a marker overlaid on the M-mode image identifying a location of the lung pulse on the M-mode image.

11. The system of claim 1, further comprising a user interface device communicatively coupled to the processor, and wherein the processor is configured to:
    receive a user input, from the user interface device, identifying a region of interest in the M-mode image; and
    generate the difference image for the region of interest in the M-mode image identified by the user input.

12. A method for detecting a lung pulse in a patient, comprising:
    obtaining, by an ultrasound probe, ultrasound imaging data representative of a lung of the patient;
    generating, by a processor communicatively coupled to the ultrasound probe and using the ultrasound imaging data received from the ultrasound probe, an M-mode image including a pleural line of the lung, the M-mode image comprising a plurality of samples obtained along a scan line;
    generating, by the processor, a difference image from the M-mode image, the difference image comprising a plurality of difference lines generated by subtracting adjacent samples of the M-mode image, each of the plurality of difference lines comprising a plurality of intensity values;
    determining, by the processor, whether the difference image includes a periodic signal representative of a lung pulse, wherein the lung pulse comprises a movement of a pleural line corresponding to a heartbeat of the patient; and
    outputting, to a display in communication with the processor, a graphical representation of detecting the lung pulse in response to determining that the difference image includes the periodic signal.

13. The method of claim 12, further comprising determining, by the processor, a location of the pleural line in the M-mode image.

14. The method of claim 12,
    wherein the difference image comprises a y-axis representative of a plurality of depths and an x-axis representative of the plurality of difference lines such that each difference line comprises a vertical line,
    wherein the plurality of intensity values is arranged along the vertical line,
    wherein the step of determining, by the processor, whether the difference image includes the periodic signal comprises:
        generating, by the processor, an axial intensity curve by summing, along each vertical line, the plurality of intensity values; and
        determining, by the processor, whether the axial intensity curve includes the periodic signal,
    the method further comprising determining, by the processor, whether the axial intensity curve includes the periodic signal by applying an autocorrelation function to the axial intensity curve.

15. The method of claim 12, wherein generating the M-mode image comprises generating the M-mode image from the scan line in each of a plurality of B-mode images obtained by the ultrasound probe over a period of time.

16. The method of claim 12, wherein obtaining the ultrasound imaging data representative of the lung of the patient comprises controlling, by the processor, the ultrasound probe to operate in an M-mode to generate the M-mode image.

17. The method of claim 12, wherein generating the difference image from the M-mode image comprises generating a plurality of first-order difference lines by subtracting immediately adjacent samples in the M-mode image.

18. The method of claim 12, wherein generating the difference image from the M-mode image comprises generating a plurality of second-order difference lines by subtracting immediately adjacent samples in the difference image.

19. The method of claim 12, wherein outputting the graphical representation to the display includes indicating at least one of a presence of the lung pulse or a period of the lung pulse, wherein the graphical representation comprises a marker overlaid on the M-mode image, the marker identifying a location of the lung pulse on the M-mode image.

20. The method of claim 12, wherein generating the difference image comprises:
   receiving, at a user interface device in communication with the processor, a user input identifying a region of interest in the M-mode image; and
   generating the difference image for the region of interest in the M-mode image identified by the user input.

* * * * *